United States Patent [19]

Moore

[11] Patent Number: 4,684,619

[45] Date of Patent: Aug. 4, 1987

[54] PROCESS FOR MAKING A DEHYDROGENATION CATALYST HAVING IMPROVED MOISTURE STABILITY

[75] Inventor: Stanley E. Moore, Lake Jackson, Tex.

[73] Assignee: The Dow Chemical Company, Midland, Mich.

[21] Appl. No.: 913,429

[22] Filed: Sep. 30, 1986

Related U.S. Application Data

[63] Continuation-in-part of Ser. No. 856,320, Apr. 28, 1986, abandoned, which is a continuation-in-part of Ser. No. 703,628, Feb. 20, 1985, abandoned.

[51] Int. Cl.[4] .............................................. B01J 23/78
[52] U.S. Cl. .................................... 502/330; 585/444
[58] Field of Search ................. 502/330; 585/444, 445

[56] References Cited

U.S. PATENT DOCUMENTS 3,703,593  11/1972  Turley et al. ....................... 502/316
4,503,163  3/1985  Chu ................................... 502/328 X Primary Examiner—W. J. Shine
Attorney, Agent, or Firm—A. Cooper Ancona

[57] ABSTRACT

A method for preparing an iron oxide containing dehydrogenative catalyst having improved moisture stability which comprises calcining by a two step method. The temperature of calcination is maintained at from about 250° to about 600° C. in the first step and from about 700° to about 800° C. in the second step. The effectiveness of the catalyst is not substantially changed from that of the single step calcination known to the art while the moisture stability is improved.

5 Claims, 1 Drawing Figure

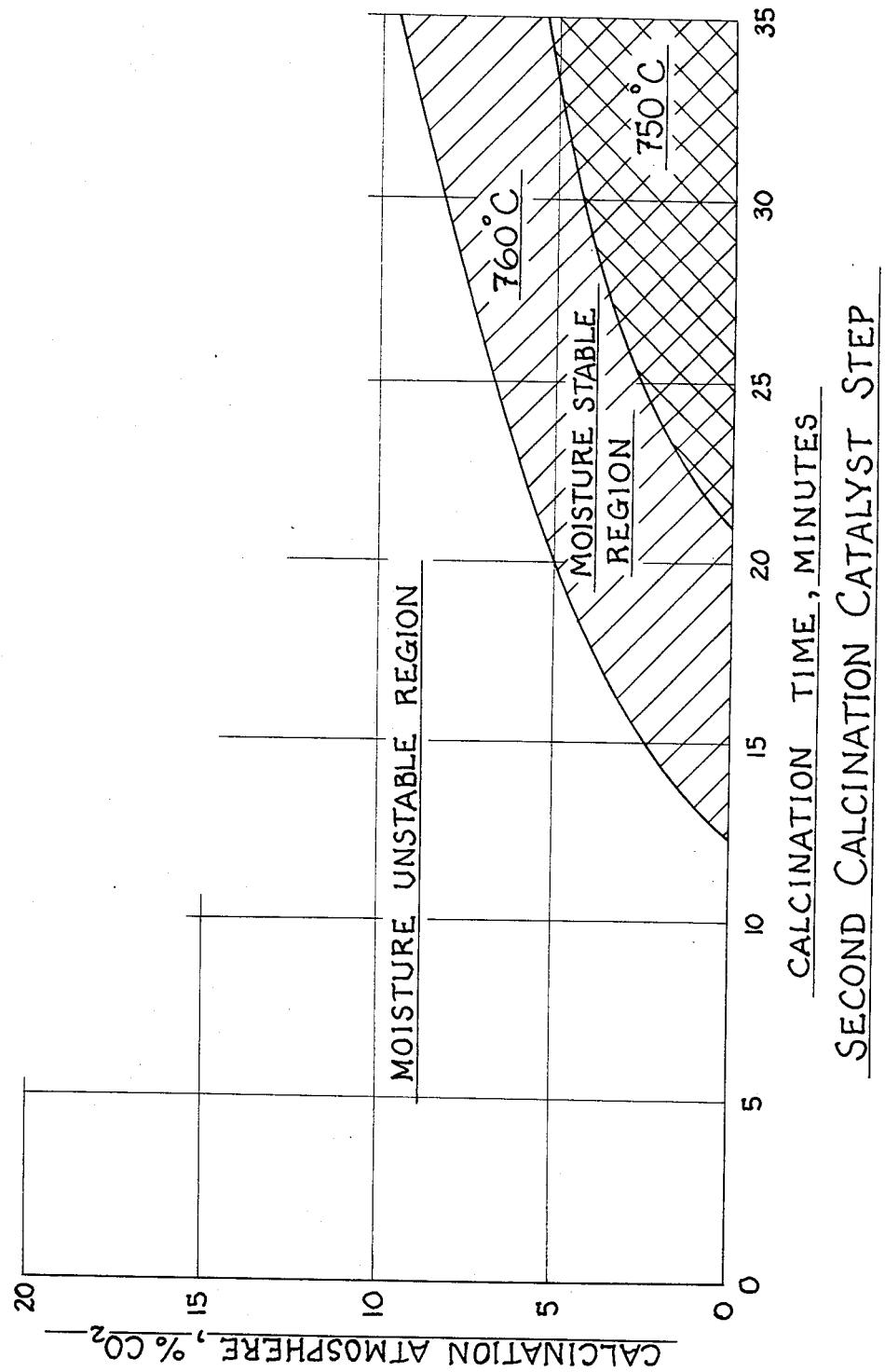

PROCESS FOR MAKING A DEHYDROGENATION CATALYST HAVING IMPROVED MOISTURE STABILITY

CROSS-REFERENCE TO RELATED APPLICATION

This application is a continuation-in-part of copending application Ser. No. 856,320, filed Apr. 28, 1986 (now abandoned) which is a continuation-in-part of application Ser. No. 703,628, filed Feb. 20, 1985 (now abandoned).

BACKGROUND OF THE INVENTION

Promoted iron oxide catalysts have been known for many years as dehydrogenation catalysts. They are especially useful in the manufacture of styrene by the dehydrogenation of ethylbenzene. Most of the catalysts now in commercial use employ minor amounts of promoters, e.g. salts or oxides of chromium, manganese, bismuth, tungsten, or molybdenum, with chromium being the preferred minor component, together with compound of potassium, e.g. potassium oxide or carbonate. The last component gives the catalyst a self-regenerative property enabling its use for long periods of time without significant loss in activity. More recent improvements include the incorporation of minor amounts of vanadium, cerium, and of modifiers (such as carbon black or graphite and methyl cellulose) which affect the pore structure of the catalysts. None of these improvements have dealt with the physical integrity of the catalysts. Improved stability to moisture is desirable while maintaining high activity and high yield.

Catalyst life of dehydrogenation catalysts is often dictated by the pressure drop across a reactor, the increase of which lowers both the yield and conversion to the desired vinyl aromatic. For this reacon, the physical integrity of the catalyst is of major importance.

In recent years catalysts with higher amounts of potassium have been used, e.g. 20% or more, up to about 48% of potassium calculated as the oxide Thus, in U.S. Pat. No. 4,503,163 catalysts are disclosed which contain 13–48% and preferably 27–41% by weight of a potassium promoter compound, calculated as potassium oxide. Such catalysts are self regenerative catalysts which perform well at lower steam to oil ratios, e.g. ratios of <2/1. The economic advantages of using less steam are obvious. Associated with the higher amounts of potassium used in such catalysts has been an increase in physical degradation due to moisture and "wet steam" during start-up conditions and plant upsets. This physical degradation can cause increased pressure drop due to coking, plugging, and reduction of the void volume in the catalyst bed.

It would be desirable if a catalyst could be prepared which had both high activity and resistance to moisture. A method has now been discovered which will provide such a catalyst.

SUMMARY OF THE INVENTION

A dehydrogenation catalyst having high activity and moisture stability has been made by a two-step calcination process in which (1) a partial calcination and removal of porosity controlling organic materials is accomplished by heating to a temperature in the range of from about 250° to about 600° C.; followed by (2) completion of calcination and conversion of alkali metal carbonates to the corresponding oxides by heating to a temperature in the range of from about 700° to about 800° C. The activity is improved if, during the second step, the $CO_2$ is removed as it evolves from the catalyst as the carbonate decomposes, allowing a shorter time at this elevated temperature.

BRIEF DESCRIPTION OF THE DRAWING

The FIGURE shows the areas encompassed by moisture stable and unstable regions when plotting the percentage of $CO_2$ in the atmosphere over the catalyst being calcined versus the calcination time at two different temperatures above which a moisture stable catalyst is obtained.

DETAILED DESCRIPTION OF THE INVENTION

Dehydrogenation catalysts of the present invention are no different with respect to chemical composition and are made from the same constituents as those of the prior art. Thus, red or yellow iron oxides can be used and the promoter materials are likewise those known to the art. Promoter compounds incorporated into the catalyst are $K_2Cr_2O_7$, $K_2CO_3$, $Cr_2O_3$, $V_2O_5$ and Co-$(OH)_2$ or other compounds of these metals such as acetates, nitrates, oxalates and the like which are reducible to their oxides. Other metal compounds which may be added as promoters include compounds of aluminum, cadmium, cerium, magnesium, manganese and nickel, providing they can be calcined to the oxide.

In addition to the catalytic components, binders and porosity agents are employed in the mixture from which the catalyst is made. A refractory cement is usually employed as a binder and carbon containing materials, such as graphite and methyl cellulose, may be used to provide porosity which is obtained when they are pyrolyzed during the manufacturing process.

The process of the present invention employs tablets or pellets of the catalytic components which materials have been dried subsequent to being pelletted or tabletted. Thereafter the first step in the process is conducted in which the carbonaceous materials which form the pores are burned out. Temperatures of from 250° to about 600° C. are employed. Temperature below 250° will not completely oxidize the carbonaceous materials and temperatures above 600° C. can cause the reduction of iron oxide as the organics burn. Above about 350° it becomes necessry to purge the catalyst environment with air in order to prevent the reduction of iron.

The chemical reactons taking place during the first calcination step can be described as follows:
(1) Cellulose pyrolization

(2) Graphite or carbon pyrolization

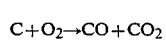

The second step in the calcination process which can follow the first without any cooling, calcines the catalyst at temperatures in the range of 700° C. to 800° C. During this calcination step, the carbonate or carbonates present are converted to the corresponding oxides.

The chemical reactions and transformations occurring during the second calcination step can be described as:
(3) Potassium carbonate decomposition

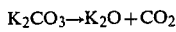

(4) Potassium ferrite formation

(5) Clay dehydroxylation and dehydration
(6) Potassium silicate formation from K-clay interaction The shorter the time required for this second step the more active the resulting catalyst. Removal of the evolved $CO_2$ from the vicinity of the catalyst during this step by providing a gas flow over the catalyst, e.g. air, shortens the time needed for carbonated decomposition and hence provides a moisture stable catalyst with no loss in activity over the moisture unstable catalyst containing the same catalytic components. The FIGURE shows the relationship between the percent $CO_2$ in the atmosphere above the catalyst during the calcination step and the time at that temperature required to provide a moisture stable catalyst. While only two temperatures are shown, the higher temperatures should provide an area of stability delineated by a line paralleling the two lower temperature indicia.

The preferred temperature for the first step is within the range of from about 350° to about 600° C. and for the second step from about 750° to about 790° C.

Time necessary for the calcination in each step will vary with the temperature employed, the higher temperatures requiring shorter times. Generally, however, from about 30 minutes to about 4 hours is sufficient time for the first step and from about 10 minutes to 60 minutes for the second step. The amount of $CO_2$ evolved and its rate of removal affects the time needed to complete this step. The time is shortened if the gases are simultaneously removed as they evolve. This is especially true in the second step where there is an equilibrium existing between the carbonate in the catalyst and the $CO_2$ in the atmosphere surrounding the catalyst.

In a representative example of making the catalyst $K_2CO_3$ is provided in an an aqueous solution to which $K_2Cr_2O_7$ is added. This solution is then mixed into a dry blend of $Fe_2O_3$, graphite, cement, clay and methyl cellulose to form a slurry which is fed to a spray drier. The slurry normally contains about 50% water, but may contain as little as 20% or as much as 70%. A preferred water content is from about 40 to about 60%. The spray dried material, which is fed to a tabletting machine, usually contains <1% water. Details of such a process are described in U.S. Pat. No. 4,139,497.

Alternatively, the mixture can be fed as a paste directly to a pelleting machine in which case the water content is from about 8 to 12%. This paste is formed as a slurry with 20 to 30% water and subsequently dried to an extrudable mass which contains the above correct water content. This alternate process is described more fully in U.S. Pat. No. 3,849,339 and U.S. Pat. No. 3,703,593.

The present invention is directed to a method of calcining such pelleted or tabletted catalyst precursors. Table I shows the composition of a number of different catalysts before calcining.

The calcining of the compositions in Table I was done by heating the catalyst pellets in a furnace up to 600° C. over a period of about one-half hour. The pellets were held at this temperature for 2 hours, then the temperature in the furnace was raised to 760° C. over a period of about one-quarter hour and then maintained at that temperature for one-half hour. The catalyst of Example 8 was calcined in the same way except that the temperature of the first step was 595° C. and that of the second step was 790° C.

TABLE I

| Example No. | $Fe_2O_3$ | $K_2CO_3$ | $K_2Cr_2O_7$ | Components (% Wt.) Cement | Graphite | CLAY | CELLULOSE | OTHER |
|---|---|---|---|---|---|---|---|---|
| 1 | 46.7 | 34.6 | 0.9 | 4.4 | 6.0 | 4.5 | 0.9 | 2.0 $ZrO_2$ |
| 2 | 45.7 | 33.9 | 0.8 | 4.2 | 4.2 | 8.4 | 0.8 | 2.0 $KHSO_4$ |
| 3 | 44.9 | 33.2 | 0.8 | 4.1 | 4.1 | 8.3 | 0.8 | 3.8 $H_3PO_4$ |
| 4 | 45.7 | 33.9 | 0.8 | 4.2 | 4.2 | 8.4 | 0.8 | 2.0 $KH_2PO_4$ |
| 5 | 46.5 | 34.5 | 0.9 | 4.3 | 4.3 | 0.0 | 0.9 | 8.6 $TiO_2$ |
| 6 | 48.7 | 36.0 | 0.9 | 4.5 | 4.5 | 0.0 | 0.9 | 4.5 $K_2B_4O_7$ |
| 7 | 34.7 | 34.2 | 0.9 | 4.5 | 4.5 | 8.9 | 0.9 | 11.4 MgO |
| 8 | 46.5 | 34.7 | 0.9 | 4.3 | 4.3 | 8.5 | 0.9 | — |

The catalysts were tested for moisture stability and for their effectiveness as dehydrogenation catalysts as follows:

DEHYDROGENATION REACTION

The catalysts shown in Table I after completing the two step calcination were placed in a laboratory reactor made of 1" OD pipe, 36" long and wrapped with beaded electrical heaters and insulated. A preheater section containing an inert column packing material preceded the catalyst bed. This assured that the ethylbenzene and water were in the vapor phase, mixed well and heated to the reaction temperature prior to contact with the catalyst. A volume of 70 ml of catalyst was provided to the reactor. Different weight ratios of steam to ethylbenzene (steam/oil, or S/O) are indicated for Examples 1–9 in Tables II and III. Each catalyst was allowed a minimum of 14 days operation as a break-in period before conversions and yields were recorded. Each of these catalysts gave adequate conversion and selectivity for the dehydrogenation of ethylbenzene to styrene.

MOISTURE TEST

The moisture stability of the catalysts was measured by the following method: Twenty pellets or tablets were placed in deionized water (sufficient to cover) and left standing for thirty minutes after which they were visually inspected for retention of shape and form. The number retaining their original form was noted and recorded as a percentage of the total used in the test, i.e. 20 tablets. For any given catalyst to pass the moisture test it must maintain 90% or greater of its original form.

Table II shows the results of moisture stability tests of the catalyst compositions from Table I after the first and second calcination steps along with the activity and selectivity as determined using the dehydrogenation reaction on each of these catalysts determined after the second calcination. The activity of the catalyst is indicated by the temperature necessary to achieve a conversion of 50%, i.e. the lower the temperature, the higher the activity.

TABLE II

CATALYST ACTIVITY AND MOISTURE STABILITY

| EXAMPLE | MOISTURE TEST Step 1 | Step 2 | 50% CONVERSION Temp.°C. | % Selectivity | S/O** |
|---|---|---|---|---|---|
| 1 | Failed | Passed | 588 | 93.6 | 1.4 |
| 2 | Failed | Passed | 589 | 93.8 | 1.0 |
| 3 | Failed | Passed | 601 | 93.2 | 1.0 |
| 4 | Failed | Passed | 594 | 93.7 | 1.0 |
| 5* | Failed | Passed | 605 | 95.0 | 1.2 |
| 6 | Failed | Passed | 603 | 94.7 | 1.4 |
| 7 | Failed | Passed | 612 | 95.0 | 1.2 |
| 8 | Failed | Passed | 593 | 94.2 | 1.0 |

*40% Conversion
**S/O is the weight ratio of steam to oil, i.e. water to ethylbenzene.

EXAMLEe 9

The catalyst of Example 8 was calcined for 2 hours at 595° C., but at different timed intervals for the second step at a temperature of 790° C. Table III shows the effect of time on the activity and selectivity of the catalyst in dehydrogenating ethylbenzene and the moisture stability of the catalyst. The temperature is that required to give 50% conversion.

TABLE III

| TIME OF SECOND CALCINATION | MOISTURE TEST After Step 2 | 50% CONVERSION Temp.°C. | % Selectivity | S/O |
|---|---|---|---|---|
| 12 min. | Failed | 586 | 94.0 | 1.0 |
| 16 min. | Passed | 596 | 93.6 | 1.0 |
| 20 min. | Passed | 598 | 93.7 | 1.0 |

EXAMPLE 10 (COMPARATIVE—ONE STEP PROCESS)

Catalyst pellets having the composition of Example 8 (Table I) were heated to the desired calcination temperature over a period of about one-half hour and then maintained at that temperature for different periods of time. The temperature and times of calcination together with results of the moisture and dehydrogenation tests are given in Table IV. The weight ratio of steam to hydrocarbon i.e. water to ethylbenzene, was 1.0. Since one of the catalysts failed the moisture test, it was not tested for dehydrogenation.

TABLE IV

| CALCINATION Temp. (°C.) | Time (hrs.) | MOISTURE TEST (Single Step) | 50% CONVERSION Temp. (°C.) | % Select. |
|---|---|---|---|---|
| 700 | 3 | Failed | — | — |
| 700 | 4 | Passed | 591 | 93.3 |
| 800 | 1½ | Passed | 605 | <93.0 |

Comparing the results in Example 10 with those of Example 8 in Table II, one sees that while the calcination using the two steps of the invention requires substantially the same temperature for 50% conversion as that using one step at 700° C. for four hours, the selectivity is nearly one percentage point difference. This is a significant advantage for the process of the invention. The difference is even more apparent when the comparison is made with the catalyst employing one step calcination at 800° C. Here both temperatures at conversion 50% and selectivity show an advantage for the process of the invention.

EXAMPLE 11

In yet another experiment the percent $CO_2$ in the atmosphere above the catalyst being calcined was measured during the second step at temperatures of 750° C. and 760° C. during timed intervals and moisture stability determined for catalysts calcined for the different times and temperatures. The results are shown in the FIGURE. Note that at 0% $CO_2$ it was necessary to heat the catalyst for about 12.5 minutes at 760° C., but a longer time of about 21 minutes was required at 750° C. At 5% $CO_2$ 20 minutes heating was required at 760° C., but between 32 and 33 minutes was required at 750° C. to obtain a moisture stable catalyst. This shows the importance of removing the $CO_2$ as it is evolved from the catalyst and of keeping the $CO_2$ concentration in the atmosphere above the calcined catalyst as low possible.

A test of two commerical scale catalysts having the same composition was conducted, one being calcined at 597° C. (Cat. A) and the other at 595° C., followed by further calcining at 785° C. in accordance with the process of the present invention (Cat. B). Results are shown in Table V:

TABLE V

| Property | Catalyst A | Catalyst B |
|---|---|---|
| Average Crush Strength | 29.6 psi | 33.4 psi |
| % Attrition | 0.19 | 0.76 |
| Water Stability* | 0% | 100% |
| Average Reactor Temperature (°C.) | 597 | 593 |
| % Conversion | 50 | 50 |
| % Selectivity | 94.0 | 94.2 |

*The water stability test was performed as previously described.

The sacrifice of some degree of attrition in a catalyst having high water stability is acceptable since the breakiang up of pellets due to water is much more severe than that caused by handling the catalyst in shipping and/or reactor loading operations.

I claim:

1. In a process for making an iron oxide-containing dehydrogenation catalyst wherein an alkali metal carbonate is employed as a promoter, organic materials are employed as porosity control agents and the constituents are combined, formed into a particulate mass and calcined at temperatures sufficient to oxidize the organic materials and convert the carbonate to an oxide, the improvement which comprises conducting the calcining process in two steps, wherein the particulate mass is heated (1) to a temperature in the range of from 250° to about 600° C. for a time of from about 30 minutes to about 4 hours which is sufficient to oxidize said organic materials and thereafter (2) to a temperature of from 700° to 800° C. for a time of from about 10 to about 60 minutes which is sufficient to convert substantially all carbonates present to the corresponding oxides.

2. The process of claim 1 wherein the products of oxidation in the first step and the carbon dioxide of the second step are removed simultaneously as they are evolved from said mass.

3. The process of claim 2 wherein the removal of evolved products of oxidation is accomplished by a flow of gas over said mass.

4. The process of claim 3 wherein the flowing gas is air.

5. The process of claim 2 wherein the temperature of steps 1 and 2 are about 350° to about 600° C. and about 750° to about 790° C., respectively.

* * * * *